United States Patent [19]

Crandall et al.

[11] Patent Number: 4,663,477

[45] Date of Patent: May 5, 1987

[54] PROCESS FOR THE HYDROLYSIS OF DIALKYL CARBONATES

[75] Inventors: John W. Crandall, Charleston; James E. Deitzler, South Charleston; Louis A. Kapicak, Cross Lanes; Fedor Poppelsdorf, Charleston, all of W. Va.

[73] Assignee: Union Carbide Corporation, Danbury, Conn.

[21] Appl. No.: 844,895

[22] Filed: Mar. 27, 1986

[51] Int. Cl.$^4$ ............................................. C07C 67/36
[52] U.S. Cl. .................................. 560/204; 560/190; 568/877; 558/277
[58] Field of Search ................ 560/204, 190; 568/877; 260/463

[56] References Cited

U.S. PATENT DOCUMENTS

| | | | |
|---|---|---|---|
| Re. 31,245 | 5/1983 | Fujii et al. | 560/193 |
| 4,410,722 | 10/1983 | Hiyazaki et al. | 560/204 |

*Primary Examiner*—Natalie Trousof
*Assistant Examiner*—Vera C. Clarke
*Attorney, Agent, or Firm*—Steven T. Trinker

[57] ABSTRACT

A process is provided for the utilization of dialkyl carbonates formed as by-products in a continuous process for the synthesis of oxalic acid esters from nitrous acid esters and carbon monoxide and wherein the esters are subsequently used as intermediates in the production of commercially useful products, such as ethylene glycol. The process comprises contacting a mixture containing the by-product comprised of a dialkyl carbonate with an aqueous solution of a metal carbonate under hydrolyzing conditions whereby the dialkyl carbonate is converted to the corresponding alkanol and the metal carbonate is converted to metal bicarbonate. Upon distillation of the alkanol from the mixture the bicarbonate is converted back to the metal carbonate which can then be recycled from the bottoms to the hydrolyzing zone for use in further hydrolysis of by-product. The alkanol is recycled for use in the continuous process.

15 Claims, No Drawings

PROCESS FOR THE HYDROLYSIS OF DIALKYL CARBONATES

FIELD OF THE INVENTION

This invention relates in general to a process for the hydrolysis of dialkyl carbonates. In one aspect, this invention is directed to a process for the utilization of dimethyl carbonate formed as a by-product in the synthesis of oxalic acid diesters. The oxalic acid esters, such as dimethyl oxalate, are useful intermediates for the preparation of commercially useful products such as ethylene gylcol. In a further aspect, the present invention relates to the hydrolysis of dimethyl carbonate to methanol wherein the dimethyl carbonate is present in the reaction mixture as a azeotrope with methanol.

BACKGROUND OF THE INVENTION

A variety of methods have been reported in the literature for the preparation of oxalic acid diesters which are useful as intermediates in the preparation of glycols and other commercially attractive compositions. One such method involves the vapor phase reaction of carbon monoxide with an ester of nitrous acid in the presence of a supported catalyst such as those containing platinum-group metals. For example, in U.S. Pat. No. Re. 31,245 which was granted May 17, 1983 and is assigned to UBE industries, Ltd., of Japan, there is disclosed and claimed a process ior the preparation of a diester of oxalic acid, such as dibutyl oxalate, by bringing carbon monoxide into contact with an ester of nitrous acid in the gaseous phase and in the presence of a solid catalyst containing metallic palladium, or a salt thereof. In those instances wherein an alcohol and nitrogen oxide or hydrate are employed in place of the nitrous acid ester, molecular oxygen can be added to the reaction system to form the ester of nitrous acid. In the examples set forth in the patent for the preparation of dibutyl oxalate, although high conversions of the butyl nitrite to the oxalate are obtained, a variety of by-products are formed as a result of the reaction, including dibutyl carbonate, butyl formate and the like.

In U.S. Pat. No. 4,410,722 which issued Oct. 18, 1983, also to UBE Industries, Ltd., of Yamaguchi Prefecture Japan, there is described a process for the preparation of oxalic acid diesters using platinum-group metals supported on alumina. In the examples, which are directed to the evaluation of certain platinum-group metals on alumina carriers having specific surface areas, it is evident that during the preparation of oxalic acid diesters, such as dimethyl oxalate, that various by-products were also present in the reaction mixture. For instance, in examples 7-11 of the patent which are directed to the preparation of dimethyl oxalate, the selectivity of the by-product, dimethyl carbonate, based on the carbon monoxide used ranged in amounts from 1.9 to 2.4 percent. Although the amount of dimethyl carbonate formed as a result of the reaction was not large compared to the selectivity of the desired dimethyl oxalate, its presence in the reaction mixture does require further purification and/or separation of the reaction mixture if it is desired that the oxalate be in a highly pure state.

Unfortunately, when the crude dimethyl oxalate is scrubbed with methanol for purification, the byproduct dimethyl carbonate forms a minimum-boiling azeotrope with methanol. The azeotrope contains about 70 percent methanol and about 30 percent dimethyl carbonate. When the tails from the scrubber go to a dimethyl oxalate refinery column, methanol is removed overhead for recycle. Thereafter, the dimethyl oxalate containing approximately 3 percent methanol goes to hydrogenation. Since dimethyl oxalate tends to break the methanol-dimethyl carbonate azeotrope, from about 50 to about 60 percent of the dimethyl carbonate goes with the dimethyl oxalate. This is, of course, desirable, because hydrogenation of dimethyl carbonate yields methanol. However, the recycled methanol stream, as opposed to the main stream, also contains dimethyl carbonate which builds up as the methanol is recycled. Hence, a method by which the dimethyl carbonate could be separated from the desired products would be advantageous. However, the economics involved in the preparation of oxalic acid diesters on a commercial scale are such that additional expensive and time consuming techniques sometimes are not justified for the removal of relatively small amounts of reaction by-products. Hence, any method by which such by-products could be removed simply and inexpensively or converted to usable products would, of course, be highly desirable.

SUMMARY OF THE INVENTION

The present invention is directed to a novel process for the hydrolysis and utilization of dialkyl carbonates which are formed as a by-product in the synthesis of dialkyl oxalates by the reaction of alkyl nitrites and carbon monoxide. The process is comprised of the following steps:

(1) contacting a mixture containing by-products comprised of a dialkyl carbonate with an aqueous solution of a metal carbonate selected from the group consisting of sodium, potassium, cesium and lithium carbonates, in a hydrolyzing zone and under hydrolyzing conditions whereby the alkyl carbonate is converted to the corresponding alkanol and the metal carbonate is converted to the metal bicarbonate, (2) heating the mixture to convert the metal bicarbonate to the metal carbonate, (3) removing as distillate the alkanol and carbon dioxide and recycling the alkanol for use in the reaction process, and (4) recycling the metal carbonate to the hydrolyzing zone.

As is evident from the above, the process of the present invention provides a simple and inexpensive method for converting by-products into useful components which can be recycled for use within the continuous process for the synthesis of oxalic acid esters.

Accordingly, the present invention provides a novel process for the hydrolysis of dialkyl carbonates formed as a by-product in the synthesis of oxalic acid diesters. In a preferred aspect, the invention provides a novel process for the hydrolysis of dimethyl carbonate in the presence of an aqueous soluton of a metal carbonate, such as potassium carbonate. By the process of the present invention it is thus possible to convert dimethyl carbonate contained in a reaction mixture to a useful product which can be recovered from a reaction stream and used in the synthesis of dimethyl oxalate.

DETAILED DESCRIPTION OF THE INVENTION

As previously indicated, the present invention provides a novel process for the hydrolysis of dialkyl carbonates, particularly dimethyl carbonate, formed as a by-product in the synthesis of dimethyl oxalate from methyl nitrite and carbon monoxide and wherein the products of the hydrolysis need not be separated but can be recycled and utilized in the overall reaction for the preparation of dimethyl oxalate. The present invention makes use of the feature that dialkyl carbonates can be hydrolyzed in the presence of metal carbonates to provide an alkanol and potassium bicarbonate. The bicarbonate itself can easily be converted back to the carbonate and hence both of the reaction products of the hydrolysis can be utilized again in the overall system for producing dialkyl oxalates. The overall reaction for the preparation of methanol from dimethyl carbonate is as follows:

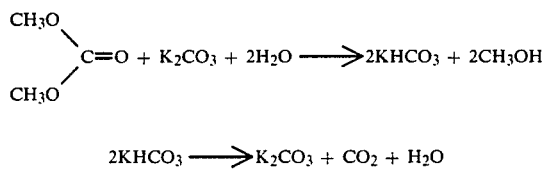

$$2KHCO_3 \longrightarrow K_2CO_3 + CO_2 + H_2O$$

In general, it has been observed that the process of the present invention can be conveniently effected by continuously hydrolyzing the dimethyl carbonate in an aqueous solution of potassium carbonate at elevated temperatures and pressures and in a hydrolyzing zone, such as a tubular reactor for periods of time sufficient to effect such hydrolysis at the particular time-temperature variables selected.

The process of the present invention, as indicated above, is useful for the hydrolysis of dialkyl carbonates formed as a by-product in the synthesis of dialkyl oxalates. Although the present invention is particularly suited for the hydrolysis of dimethyl carbonate, other lower alkyl carbonates can also be hydrolyzed in a similar manner. Hence, the present invention can be utilized in the hydrolysis of dialkyl carbonates having from 1 to 4 carbon atoms in the alkyl group. Illustrative of such carbonates are ethyl, propyl, and butyl carbonates.

The metal carbonates employed in the process of this invention are those which under the hydrolyzing conditions are converted to the corresponding bicarbonate and thereafter upon distillation are converted back to the metal carbonate. Suitable metal carbonates include sodium potassium, cesium and lithium carbonate.

In practice it has been found that temperatures within the range of from about 70° to about 150° C. and pressures of from about 5 to about 200 psig are usually sufficient to effectively hydrolyze the dimethyl carbonate present in the reaction mixture. Temperatures of form about 40° to about 100° C. and pressures of from about 25 to about 45 psig are preferred. In actual operation, excellent hydrolysis of the dimethyl carbonate is achieved when a temperature of about 100° C. is employed and the reaction is conducted in a tubular reactor at a pressure of about 45 psig.

As indicated, the required residence time in the reactor will vary as a function of the temperature and pressure. However, for the most part, a residence time of from 120 to 3 minutes is usually sufficient and a residence time for from about 10 to about 20 minutes is preferred. Under actual operating conditions at the 100° C. temperature and the 45 psig pressure, a residence time of approximately 15 minutes has been found adequate.

The potassium carbonate is employed in the process of the present invention as an aqueous solution. In practice, the potassium carbonate is present in an amount at least sufficient to hydrolyze all the dimethyl carbonate present so that the dimethyl carbonate is converted to methanol, carbon dioxide and water. It has been discovered that optimum results are obtained if the potassium carbonate is present in excess. For example, if a twenty percent aqueous potassium carbonate solution is employed, such that a 20 percent excess of the carbonate is present over that theroetically required, excellent conversion of the by-product to methanol is obtained.

An outstanding advantage of the process of the present invention, is that for each mole of the dimethyl carbonate present as the by-product, two moles of methanol are obtained and all of the potassium carbonate can also be regenerated for reuse. If any methyl formate is present, one mole of methanol is obtained upon hydrolysis and one-half mole of potassium carbonate is recovered. Under such conditions, that is, where methyl formate is present as a by-product, some make-up potassium carbonate might be required.

In the purification of dimethyl oxalate by distillation of a synthetic feed composed of approximately 81percent dimethyl oxalate, 4 percent dimethyl carbonate and 15 percent methanol, it was found that about 40 percent of the dimethyl carbonate was distilled overhead with the methanol and 60 percent remained with the dimethyl oxalate bottoms product. Although the use of the metal carbonates mentioned above results in excellent conversion, and the metal carbonates have the added feature that they can be regenerated and recycled for hydrolysis of additional dimethyl carbonate, the use of potassium carbonate is preferred since aqueous solutions of potassium carbonate have a greater solubility in organic compounds than certain of the other metal carbonates, such as sodium carbonate.

As indicated in the equation above, one mole of dimethyl carbonate is converted into 2 moles of methanol with the formation of 2 moles of potassium bicarbonate. Upon distillation of the mixture, potassium bicarbonate is decomposed to potassium carbonate, carbon dioxide and water. The methanol and carbon dioxide are removed overhead and aqueous potassium carbonate is removed as bottoms product.

The novel process of the present invention, as herein before indicated, is particularly useful for recovery of methanol values from dimethyl carbonate formed as a by-product in the synthesis of dimethyl oxalate from methyl nitrite and carbon monoxide. The dimethyl carbonate formed in the reaction is present in the mixture with dimethyl oxalate and methanol and possibly other by-products such as methyl formate. The novel process of the present invention can easily be incorporated into the overall system and as a result of the conversion of the undesired by-product to useful methanol, and regeneration and recycling of the potassium carbonate, increased savings in the operation of the system are achieved.

In operation, the distillate from the dimethyl oxalate refining column is fed to an azeotrope column wherein dimethyl carbonate and any methyl formate are concentrated overhead in methanol and the tails from the same column are recycled methanol. Thereafter, the distillate from the azeotrope column is hydrolyzed by adding potassium carbonate to the methanol solution containing the dimethyl carbonate and methyl formate and passing the resulting mixture through a tubular reactor at a temperature of about 100 C. and at a pressure of about 60 psig for a residence time of about 15 minutes. The mixture is then fed to a flash distillation unit wherein the distillate, water and methanol go to a dehydration column for the recovery of methanol. The tails from the flash distillation, mainly aqueous potassium carbonate, are recycled to the reactor for use in the hydrolysis step. Due to the consumption of water in the hydrolysis reaction and the loss of water in the flash distillation, it will be necessary to add make-up water to balance the system. Oxalic acid diesters are useful as intermediates for the synthesis of a variety of compounds. For example, ethylene glycol is conveniently prepared by the vapor phase hydrogenation of oxalate esters such as dibutyl oxalate in the presence of suitable hydrogenation catalysts as described in U.S. Pat. No. 4,112,245 which issued Sept. 5, 1978 to L. R. Zehner et al.

The following examples illustrate the present invention:

EXAMPLE 1

HYDROLYSIS OF DIMETHYL CARBONATE

A feed consisting of 80 percent by weight of methanol, 10 percent dimethyl carbonate, and 10 percent methyl formate was mixed with aqueous 20 percent potassium carbonate. A 20 molar percent excess of potassium carbonate was used. Thereafter, the mixture was pumped through a tubular reactor at 97° C. and 60 psig pressure, and then fed to a flash distillation unit at atmospheric pressure. Residence time in the reactor was 15 minutes. Analysis of the distillate and bottoms from the flash distillation are set forth below in Table I. The figures in the table are in percent by weight.

It will be evident from the data set forth in Table I that both methyl formate and the dimethyl carbonate had been hydrolyzed under the reaction conditions and that the amount of usable methanol had increased.

TABLE I

| Component | Distillate | Bottoms |
|---|---|---|
| Methyl formate | nil | nil |
| Methanol | 77.2 | 5.5 |
| Dimethyl carbonate | 0.6 | nil |
| Water | 21.9 | 77.3 |
| Potassium carbonate | — | 15.2 |

EXAMPLE 2

HYDROLYSIS OF DIMETHYL CARBONATE

In a manner similar to that employed in Example 1, a feed consisting of equal weights of (a) 95 percent methanol and 5 percent dimethyl carbonate, and (b) an aqueous solution containing 7.5 percent by weight of potassium carbonate were mixed and pumped through a tubular reactor at 95°–100° C. and 60–75 psig pressure. The residence time in the reactor was 1 hour. The mixture was then fed to a flash distillation unit at atmospheric pressure. After flash distillation, 336 grams of distillation product was obtained at 73°–86° C. and 212 grams of residue product obtained at 81°–96° C. The analysis of the flash distillation products were as follows:

TABLE II

| component | Flash Distillate | Flash Residue |
|---|---|---|
| Water | 24.62 | 87.6 |
| Methanol | 75.00 | 3.5 |
| Dimethyl carbonate | 0.07 | nil |
| Potassium carbonate | N.A. | 8.1 |

Figures are in percent by weight.

Thereafter, the 212 grams residue was mixed with 215 grams of a fresh mixture of equal weights of 95 percent methanol and 5 percent dimethyl carbonate and the mixture pumped through a tubular reactor under the same conditions except that the residence time was changed to 31 minutes. After flash distillation the analyses of the products were as follows:

TABLE III

| Component | Flash Distillate | Flash Residue |
|---|---|---|
| Water | 18.2 | 83.5 |
| Methanol | 81.1 | 3.6 |
| Dimethyl carbonate | 0.5 | nil |
| Potassium carbonate | N.A. | 11.5 |

It is evident from the above data that the potassium carbonate is regenerated and can therefore be recycled for use in a continuous reaction system.

EXAMPLE 3

In a manner similar to the preceding examples, another feed consisting of 28 percent by weight of (a) 70 percent methanol and a 30 percent aqueous solution of dimethyl carbonate was mixed with (b) a 71 percent by weight of an aqueous solution containing 20 percent potassium carbonate. The mixture was pumped through a tubular reactor at 97° C. and 60 psig pressure, and then fed to a flash distillation unit at atmospheric pressure. Residence time in the reactor was 14 minutes. After flash distillation 194 grams of distillate was obtained, and the remainder residue. Analyses of the flash distillation products were as follows:

TABLE IV

| Feed | Distillate | residue |
|---|---|---|
| Water 56.8(294.2 gms) | 23.7(46.0 gms) | 72.6(235.2 gms) |
| Methanol 20.3(105 gms) | 75.0(145.5 gms) | 3.2(10.4 gms) |
| Dimethyl carbonate 8.7(45.1 gms) | 1.1(2.1 gms) | nil |
| Potassium carbonate 14.2(73.6 gms) | N.A. | 22.0(71.3 gms) |

From the above data it can be noted that essentially all of the dimethyl carbonate was converted to methanol, the potassium carbonate was regenerated and the residence time was reduced.

Although the invention has been illustrated by the preceding examples, it is not to be construed as being limited to the materials employed therein, but rather, the invention is directed to the generic area as hereinbefore disclosed. Various modifications and embodiments thereof can be made without departing from the spirit or scope thereof.

What is claimed is:

1. In a continuous process for the synthesis of oxalic acid diesters by the reaction of an ester of nitrous acid and carbon monoxide to form an intermediate mixture containing an oxalic acid diester and undesirable reaction by-products, and wherein said oxalic acid diester is subsequently processed into commercially useful products, the improvement which comprises converting and recycling said by-products comprised of a dialkyl carbonate having from 1 to 4 carbon atoms in each alkyl group, by the steps of:

(1) contacting a mixture containing said by-products comprised of said dialkyl carbonate with an aqueous solution of a metal carbonate, selected from the group consisting of potassium, sodium, cesium and lithium carbonate, in a hydrolyzing zone and under hydrolyzing conditions whereby said dialkyl carbonate is converted to the corresponding alkanol and said metal carbonate is converted to said metal bicarbonate, (2) distilling said mixture to convert said metal bicarbonate to said metal carbonate, (3) removing as distillate said alkanol and carbon dioxide, and recycling said alkanol for use in said continuous process, and (4) recycling said metal carbonate to said hydrolyzing zone.

2. The process of claim 1 wherein said ester of nitrous acid is methyl nitrite.

3. The process of claim 1 wherein said by-product is methyl carbonate.

4. The process of claim 1 wherein said by-product is a mixture of methyl carbonate and methyl formate.

5. The process of claim 1 wherein said by-product is ethyl carbonate.

6. The process of claim 1 wherein said by-product is propyl carbonate.

7. The process of claim 1 wherein said byproduct is butyl carbonate.

8. The process of claim 1 wherein said metal carbonate is potassium carbonate.

9. The process of claim 1 wherein said metal carbonate is sodium carbonate.

10. The process of claim 1 wherein said metal carbonate is cesium carbonate.

11. The process of claim 1 wherein said metal carbonate is lithium carbonate.

12. The process of claim 1 wherein said aqueous solution of metal carbonate contains about 20 percent by weight of potassium carbonate.

13. The process of claim 12 wherein said potassium carbonate is employed in a molar excess of that required to convert all of the dialkyl carbonate present to the corresponding alkanol.

14. The process of claim 1 wherein said hydrolyzing zone is a tubular reactor.

15. In a continuous process for the synthesis of oxalic acid diesters by the reaction of an ester of nitrous acid and carbon monoxide to form an intermediate mixture containing an oxalic acid diester and undesirable reaction by-products, and wherein said oxalic acid diester is subsequently processed into commercially useful products, the improvement which comprises converting and recycling said by-products comprised of at least methyl carbonate by the steps of:

(1) contacting a mixture containing said by-products comprised of methyl carbonate with an aqueous solution of potassium carbonate, in a hydrolyzing zone and under hydrolyzing conditions whereby said methyl carbonate is converted to methanol and said potassium carbonate is converted to potassium bicarbonate, (2) distilling said mixture to convert said potassium bicarbonate to potassium carbonate, (3) removing as distillate methanol and carbon dioxide, and recycling said methanol for use in said continuous process, and (4) recycling said potassium carbonate to said hydrolyzing zone.

* * * * *